(12) United States Patent
Ophardt (10) Patent No.: US 11,366,055 B2
(45) Date of Patent: Jun. 21, 2022

(54) BUBBLE COMPOSITION ANALYSIS

(71) Applicant: OP-Hygiene IP GmbH, Niederbipp (CH)

(72) Inventor: Heiner Ophardt, Arisdorf (CH)

(73) Assignee: OP-Hygiene IP GmbH, Niederbipp (CH)

( * ) Notice: Subject to any disclaimer, the term of this patent is extended or adjusted under 35 U.S.C. 154(b) by 41 days.

(21) Appl. No.: 16/931,573

(22) Filed: Jul. 17, 2020

(65) Prior Publication Data

US 2021/0025812 A1 Jan. 28, 2021

Related U.S. Application Data (60) Provisional application No. 62/879,062, filed on Jul. 26, 2019.

(51) Int. Cl.
| | | |
|---|---|---|
| *G01N 21/31* | (2006.01) | |
| *G01N 33/00* | (2006.01) | |
| *G01N 21/25* | (2006.01) | |
| *G01N 21/33* | (2006.01) | |

(52) U.S. Cl.
CPC .......... *G01N 21/31* (2013.01); *G01N 21/255* (2013.01); *G01N 21/33* (2013.01); *G01N 33/0039* (2013.01)

(58) Field of Classification Search
None
See application file for complete search history.

(56) References Cited

U.S. PATENT DOCUMENTS

| | | | |
|---|---|---|---|
| 4,849,178 A * | 7/1989 | Azuma | G01N 21/33 422/69 |
| 7,236,243 B2 | 6/2007 | Beecroft et al. | |
| 8,672,187 B2 | 3/2014 | Ophardt | |
| 8,733,596 B2 | 5/2014 | Ophardt et al. | |
| 9,149,161 B2 | 10/2015 | Ophardt et al. | |
| 9,936,841 B2 | 4/2018 | Ophardt et al. | |
| 2003/0234928 A1* | 12/2003 | Lucas | C23C 2/003 356/318 |
| 2018/0224357 A1* | 8/2018 | Hintz | G01N 21/3577 |

OTHER PUBLICATIONS https://chem.libretexts.org/Bookshelves/Analytical_Chemistry/Book%3A_Analytical_Chemistry_2.0_(Harvey)/10_Spectroscopic_Methods. David Harvey. Jul. 25, 2019. Web Pages: 10: Spectroscopic Methods—Page ID 3479 (2 pgs); 10.1: Overview of Spectroscopy—Page ID: 5608 (12 pgs); 10.2: Spectroscopy Based On Absorption—Page ID: 5609 (8 pgs); 10.3: UV/VIS and IR Spectroscopy—Page ID: 5610 (27 pgs).

* cited by examiner

*Primary Examiner* — Shawn Decenzo
(74) *Attorney, Agent, or Firm* — Thorpe North & Western, LLP (57) ABSTRACT

A method of spectroscopically assessing the chemical composition of a bubble while the bubble constrains a gas within the interior of the bubble by passing light passing through the bubble and comparing properties of the light before and after the light has passed through the bubble. The bubble is located, preferably compressed between a first plate and a second plate providing a compressed bubble with relatively flat first polar end wall portion adjacent the first plate in a relatively flat second polar end wall portion adjacent a second plate and directing the light to pass through the bubble via the first and second polar end wall portions.

20 Claims, 6 Drawing Sheets

BUBBLE COMPOSITION ANALYSIS

SCOPE OF THE INVENTION

This invention relates to a method and apparatus for assessing the composition of a bubble.

BACKGROUND OF THE INVENTION

Bubbles are known having a wall of liquid enclosing a gas within the interior of the wall.

The applicants have appreciated the disadvantages that no practical methods or apparatuses are known for the measurement of the composition of a bubble as, for example, to determine the concentration of compounds in the bubble such as within the gas contained within the bubble.

Ozonated foams are known for disinfecting and cleaning purposes, as with the ozonated foams are applied to a surface to be cleaned as, for example, as disclosed in U.S. Pat. Nos. 8,672,187; 8,733,596; 9,149,161 and 9,936,841, each having as an inventor, Heiner Ophardt and whose disclosures are incorporated herein. The ozonated foams are foamed by passing ozonated air and a foamable liquid through a foam generator to produce a foam comprising bubbles of the liquid encapsulating within the interior of the bubble the ozonated air. Used as a hand cleaner, the ozonated foam is discharged onto a person's hands for cleaning of the surface of the hands. The applicants have appreciated the disadvantage that no practical arrangements are known for measurement of the concentration of the ozone in the ozonated foam, nor of the concentration of the ozone gas in the gas within the bubbles in the foam.

Ozone gas is known to be a strong oxidizer and to be reduced to oxygen. Ozone gas in atmospheric air under typical ambient conditions is expected to have a relatively short half-life of, for example, three days in 20° C. air. Ozone gas when dissolved in pure water is expected to have a half-life of about 20 minutes at 20° C.

The applicants have appreciated that ozone gas may decompose more promptly based on the nature of the other compounds it comes into contact with and in the context of foams, these other compounds include the various compounds that may be provided within the foamable liquid such as foaming agents and surfactants.

The applicants have appreciated the disadvantage that the ozone gas contained in the bubbles of an ozone foam will change in concentration with time, sometimes very promptly.

The applicants have appreciated the disadvantage that the concentration of ozone gas within a bubble in an ozone foam cannot be accurately measured by collapse of the bubbles and the absorption of the ozone into a liquid since the ozone gas that existed in the bubble may largely decompose in the collapse of the bubble and absorption with the liquid.

SUMMARY OF THE INVENTION

To at least partially overcome these disadvantages of previously known devices, the present invention provides a method of assessing the composition of a bubble and, more particularly, a method of spectroscopically, preferably optically spectroscopically, assessing the chemical composition of a bubble while the bubble constrains the gas within the interior of the bubble.

In accordance with the present invention, a bubble is located, preferably but not necessarily constrained, between a first plate and a second plate, electromagnetic radiation, preferably light, is directed through the bubble and the light passing through the bubble has one or more of its properties measured for comparison between the light emitted and the light that has passed through the bubble for use in estimating the composition of the bubble.

In a preferred arrangement, the bubble is generated having a typically spherical liquid bubble wall forming a bubble interior compartment enclosing a gas, with the bubble wall having an exterior bubble diameter. The method involves compressing the bubble between a first plate and a second plate providing a compressed bubble with relatively flat first polar end wall portion adjacent the first plate in a relatively flat second polar end wall portion adjacent a second plate and directing the emitted light to pass through the bubble via the first and second polar end wall portions.

Preferably, the first plate and second plate are spaced apart a distance less than the bubble diameter, more preferably, in the range of 60% to 90% of the bubble diameter.

Preferably, the compressed bubble has a generally disc-shaped compressed bubble wall including an annular equatorial wall portion bridging between the first polar end wall portion adjacent the first plate and the second polar end wall portion adjacent the second plate.

Preferably, the first plate provides a first surface to be engaged by the bubble which is disposed in a flat plane and the second plate includes a second surface to be engaged by the bubble in a second flat plane normal to the first flat plane.

Preferably, to provide a first plate and a second plate spaced a desired distance from each other, one or more spacers are provided between the first surface and the second surface which, when the first plate and the second plate are forced towards each other, will space the first surface and the second surface the desired distance.

Preferably, the properties of the electromagnetic radiation, preferably light, are measured optically as, for example, by knowing or measuring properties of the light that is emitted and measuring properties of the light that have passed through the bubble and comparing the differences. For example, in a preferred embodiment, the method involves using spectroscopic methods, preferably optical spectroscopic methods, as with a spectroscope for producing and observing a spectrum of electromagnetic radiation such as light from the emitted light as, for example, when emitted and after being passed through the compressed bubble and then comparing the various spectrum in manners known to persons skilled in the art. The spectrum may be analysed to assess whether light of specific wavelengths have been absorbed indicating, for example, the presence of one or more particular compounds. The light emitted may comprise a wide spectrum of light or radiation or may comprise light or radiation of specific wavelengths, for example, selected to be absorbed by a compound or compounds that the method is designed to identify or quantify. For example, insofar as a particular compound is being looked for in the bubble, the emitter may emit light in a range of wavelengths that is selectively absorbed by the compound being looked for and the intensity of the light that has passed through the compressed bubble can provide an indication as to the concentration of the compound in the bubble.

When the compound being looked for is ozone gas, the emitted light can be limited to wavelengths that are selectively absorbed by the ozone gas including preferably wavelengths in the range of about 200 nm to about 310 nm with a preferred wavelength being 250 nm which is known to be absorbed by ozone gas.

Preferably, the emitted light is polarized and/or emitted by a laser so as to pass as parallel light waves through the bubble.

In accordance with the present invention, when a bubble is retained between the first plate and the second plate, preferably, each of the first polar end wall portion and the second polar end wall portion is substantially planar and disposed in the same plane as the first surface of the first plate and the second surface of the second plate, respectively. This is advantageous such that the emitted light may be passed through the first polar end wall and the second polar end wall and with the extent to which the first polar end wall and the second polar end wall are disposed flat and parallel to each other reducing the extent to which the light emitted is diffused by the first and second equatorial end wall portions being curved.

In a preferred arrangement, the first equatorial end wall portion and the second equatorial end wall portion are each circular as by having a perimeter that appears circular, or at least substantially circular, about a central axis normal to the first surface of the first plate and the second surface of the second plate. Such central axis passes through a first central point of the first polar end wall portion and a second center point of the second polar end wall portion. A method in accordance with the present invention preferably includes locating as on the first plane of the first plate, a center position that coincides with the center point of the first polar end wall portion. Preferably, the emitted light is passed through the bubble proximate the center portion on the first plate and preferably normal to the first surface of the first plate.

The method preferably includes providing a plate holding structure carrying the first plate and the second plate and a light directing holding structure that directs the emitted light with the plate holding structure and the light directing holding structure being movable relative to each other and thereby providing for adjusting of the relative location of the plate holding structure and the light directing holding structure, for example, having regard to the center position on the first plane of the first plate to direct the emitted light to pass through the first and second polar end wall portions of the bubble.

In accordance with the present invention, one or more of the first surface and the second surface may comprise a mirror surface for reflecting the emitted light. In accordance with the present invention, one or more of the first surface and the second surface may be provided with structures to locate a bubble in a desired location as, for example, with one or more openings through the first plate and/or the second plate which will engage a bubble to locate the bubble coaxially with the openings.

The invention also provides a method including generating one or more bubbles by forcing a foamable liquid together with a gas through a foam generator.

The invention also provides an apparatus for optically assessing the chemical composition of a bubble, or a plurality of bubbles and, preferably, for generating one or more bubbles by forcing a foamable liquid together with a gas through a foam generator.

In accordance with one aspect of the present invention, the invention provides a hand cleaner dispenser for dispensing a foam of a foamable liquid and a gas, preferably ozone, onto a person's hands for cleaning and/or disinfecting the hands which dispenser includes an apparatus for receiving a sample of the foam dispensed, forming a bubble or a plurality of bubbles, and optically assessing the chemical composition of the bubble by passing light through a single or a plurality of bubbles. In one arrangement, the bubble or bubbles, or at least some proportion of the bubbles are constrained into a single layer of the bubbles.

The present invention also provides a method of optically assessing the chemical composition of a bubble by creating a single layer of bubbles, compressing at least one bubble in a single layer so as to provide relatively flattened polar end portions of the bubble wall and passing light through the bubble via the polar end wall portions.

Ozonated foam is but one example of a foamed liquid that has a bubble and in which it is desired to determine the composition of the bubble and, more particularly, the composition of the gas, such as ozone, within a bubble. The inventors have appreciated that the formation of a foam by the passage of a gas and a foaming liquid through a foam generator can be used as a means to constrain within the bubbles the gas which may be desired to be analysed. The gas may then be analysed in accordance with the bubble composition analysis of the method and apparatus in accordance with the present invention thus providing a mechanism for capture of the gas within a bubble and an analysis of the gas within a bubble which provides a relatively simple method for bubble composition analysis. The method is adapted to be carried out in a variety of apparatus including a relatively simple hand held bubble analysis apparatus, particularly when a particular gas is searched for in a bubble.

In accordance with some aspects of the invention, a bubble or bubbles are located between a first surface and a second surface and electromagnetic radiation passed through the bubbles. Preferably, the first surface and the second surface are spaced a distance apart that is not greater than a diameter of a bubble desired to be analysed, more preferably, less than 100% of the bubble diameter, often preferably between 60% and 90% of the bubble diameter. However, having the first and second surfaces spaced no greater than the bubble diameter is one preferred arrangement but not necessary. In accordance with the present invention, a foam of bubbles may be generated and the foam located between first and second surfaces spaced greater than a desired median size of the bubbles, to constrain the bubbles towards forming a single layer of bubbles. As well, rather than attempt to constrain the bubbles into a single layer of bubbles, the first surface and the second surface may constrain the bubbles into a relatively small number of layers of bubbles, as by spacing the first surface and the second surface not greater than 200% or 300% or 500% or 1000% of a desired median bubble diameter. The spacing of the first surface and the second surface is to be selected to permit the electromagnetic radiation to pass through the bubbles as for measuring selective absorption of a specific wavelength.

In one aspect, the present invention provides a method of optically assessing the chemical composition of a bubble comprising the steps of:

a) generating a bubble having a liquid bubble wall forming a bubble interior compartment enclosing a gas, b) emitting electromagnetic radiation, preferably light, having at least one property, c) passing the emitted light through the bubble to pass the emitted light through both the bubble wall and the bubble interior compartment, d) measuring the property of the emitted light after it has passed through the bubble, e) comparing the measured property of the emitted light after it passes through the bubble with the property of the emitted light before it passes through the bubble, f) estimating based on the results of the comparing step (e) the chemical composition of the spherical bubble.

In a $2^{nd}$ aspect, the present invention provides a method as in the $1^{st}$ aspect wherein the bubble is generated as a spherical bubble with the bubble wall being spherical and having an exterior bubble diameter, g) locating the bubble in a gap formed between a first surface and an opposing second surface spaced a distance less than the bubble diameter, preferably in a range of 60% to 90% of the bubble diameter, with the bubble engaging both the first surface and the second surface, and passing the emitted light through the bubble while the bubble is located in the gap.

In a $3^{rd}$ aspect, the present invention provides a method as in the $1^{st}$ aspect, wherein the bubble is generated as a spherical bubble with the bubble wall being spherical and having an exterior bubble diameter, g) locating the bubble in a gap formed between a first surface and an opposing second surface spaced a distance less than the bubble diameter with the bubble engaging both the first surface and the second surface with a first polar end wall portion of the bubble wall engaging the first surface wall lying in the plane of the first surface and a second polar end wall portion of the bubble wall engaging the second surface lying in the plane of the second surface with an annular equatorial wall portion of the bubble wall spanning between the first surface and the second surface and bridging between the first end wall portion and the second end wall portion, and passing the emitted light through the bubble while the bubble is located in the gap.

In a $4^{th}$ aspect, the present invention provides a method as in the $3^{rd}$ aspect, wherein passing the emitted light in sequence through the first polar end wall portion of the bubble wall, through the bubble interior compartment and through the second polar end wall portion of the bubble wall.

In a $5^{th}$ aspect, the present invention provides a method as in any one of the $2^{nd}$ to $4^{th}$ aspects wherein the second surface is parallel to the first surface.

In a $6^{th}$ aspect, the present invention provides a method as in any one of the $2^{nd}$ to $5^{th}$ aspects including passing the emitted light through the bubble in a direction normal to the first surface.

In a $7^{th}$ aspect, the present invention provides a method as in any one of the $2^{nd}$ to $6^{th}$ aspects including providing the gap between a first plate providing the first surface and a second plate providing the second surface.

In an $8^{th}$ aspect, the present invention provides a method as in the $7^{th}$ aspect including providing the bubble between the first plate and the second plate while the first surface and the second are spaced a distance greater than the bubble diameter and moving the first plate and the second plate towards each other to locate the first surface and the second spaced the distance less than the bubble diameter compressing the bubble therebetween to form a compressed bubble with the first polar end wall portion of the bubble wall engaging the first surface wall lying in the plane of the first surface and the second polar end wall portion of the bubble wall engaging the second surface lying in the plane of the second surface with the annular equatorial wall portion of the bubble wall spanning between the first surface and the second surface and bridging between the first end wall portion and the second end wall portion.

In a $9^{th}$ aspect, the present invention provides a method as in the $8^{th}$ aspect including stopping movement of the first plate and the second plate towards each other to locate the first surface and the second spaced the distance less than the bubble diameter by engagement between one or more spacer members provided between the first plate and the second plate.

In a $10^{th}$ aspect, the present invention provides a method as in the $8^{th}$ or $9^{th}$ aspects including locating on the first surface a center of the first polar end wall portion, and directing the emitted light to pass through the center.

In an $11^{th}$ aspect, the present invention provides a method as in the $10^{th}$ aspect including directing the emitted light to pass through the center by moving the first plate and the second plate while fixed together as a unit with the bubble compressed therebetween relative to an emitter for the emitted light such that the emitted light passes through the center.

In a $12^{th}$ aspect, the present invention provides a method as in the $7^{th}$ aspect including moving the bubble between an upstream portion between the first plate and the second plate in which the first plate and the second plate are spaced a distance greater than the bubble diameter into the gap compressing the bubble as it is moved into the gap.

In a $13^{th}$ aspect, the present invention provides a method as in the $12^{th}$ aspect including moving the bubble from the gap downstream between the first plate and the second plate toward a discharge outlet.

In a $14^{th}$ aspect, the present invention provides a method as in the $1^{st}$ aspect including generating the bubble as one of a plurality of spherical bubbles each having its respective bubble wall of an exterior bubble diameter, constraining the bubbles in a space formed between a first surface and an opposing second surface spaced a distance not greater than 10 times the diameters of the bubbles, and passing the emitted light through the space while the bubbles are located in the space.

In a $15^{th}$ aspect, the present invention provides a method as in any one of the $1^{st}$ to $14^{th}$ aspects to assess the presence of ozone within a bubble of a foamable aqueous fluid, the emitted light including light of a wavelength that is absorbed by ozone, measuring light of the wavelength of the emitted light after it has passed through the bubble, comparing the measured light of the wavelength of the emitted light after it has passed through the bubble with the light of the wavelength of the emitted light before it passes through the bubble, and estimating based on the results of the comparing the presence of ozone in the bubble.

In a $16^{th}$ aspect, the present invention provides a method as in the $15^{th}$ aspect including generating the bubble by passing a mixture of air and the fluid through a foam generator to produce a foamed mixture of the air and the fluid containing the bubble.

In a $17^{th}$ aspect, the present invention provides a method as in any one of $2^{nd}$ to the $13^{th}$ aspects including:

providing the first plate to have a first opening therethrough circular about an axis, with the first opening having a first diameter about the axis less than the spherical bubble diameter, providing the compressed bubble between the first plate and the second plate with the first end wall portion coaxial about the axis, with the first end wall portion in engagement with the first plate annularly about the first opening, directing the emitted light to pass through the through the first plate via the first opening.

In an $18^{th}$ aspect, the present invention provides a method as in the $17^{th}$ aspect wherein the first opening has a diameter not greater than ½ of the bubble diameter.

In a 19th aspect, the present invention provides a method as in the 17th or 18th aspect including providing the second plate to have a second opening therethrough circular about the axis opposed to the first opening and the second opening having a second diameter about the axis less than the spherical bubble diameter, providing the compressed bubble between the first plate and the second plate and with the second end wall portion coaxial about the axis, with the second end wall portion in engagement with the second plate annularly about the first opening, directing the emitted light to pass through the second plate via the second opening.

In a 20th aspect, the present invention provides a method as in the 19th aspect wherein the second opening has a diameter not greater than ½ of the bubble diameter.

In a 21st aspect, the present invention provides a method as in the 5th aspect including providing the surface of the second plate to have a mirrored surface that is reflective of the emitted light, directing the emitted light to pass through the first plate, through the bubble to reflect off the mirrored surface of the second plate, pass and back through the bubble and through the first plate to provide emitted light that has passed through the bubble.

In a 22nd aspect, the present invention provides a method as in any one of the 1st to 21st aspects wherein the emitted light is polarized.

In a 23rd aspect, the present invention provides a method of optically assessing the chemical composition of a plurality of bubbles comprising:

generating bubbles, each having a liquid generally spherical bubble wall forming a bubble interior compartment enclosing a gas, the bubble wall having an exterior bubble diameter, constraining the bubbles between a first surface and a second surface, emitting light, directing the emitted light to pass through the bubbles, measuring differences in properties of the light that has passed through the bubbles compared to properties of the light emitted, estimated based on the differences measured, a chemical composition of the bubble.

In a 24th aspect, the present invention provides a method as in the 23rd aspect wherein the first plate and the second plate are spaced a distance selected from the group of:

not greater than 60% of a desired median exterior bubble diameter;

not greater than 200% of the median of the exterior bubble diameter;

not greater than 300% of the median of the exterior bubble diameter; and not greater than 1000% of the median of the exterior bubble diameter.

In a 25th aspect, the present invention provides a method as in the 23rd or 24th aspect including collecting emitted light passing through the bubbles and comparing the intensity of a specific wavelength of light in the light emitted to the intensity of the specific wavelength of light in the light collected as a factor in estimating whether the bubbles include a compound that absorbs the specific wavelength.

BRIEF DESCRIPTION OF THE DRAWINGS

Further aspects and advantages of the present invention will appear from the following description taken together with the accompanying drawings in which.

DETAILED DESCRIPTION OF THE DRAWINGS

Reference is made to FIGS. 1 to 4 illustrating a first embodiment of a bubble analysis apparatus 10 in accordance with the present invention. The bubble analysis apparatus 10 includes a bubble holding mechanism 12 and an optical analysis system 14, only schematically shown.

Figure 2:
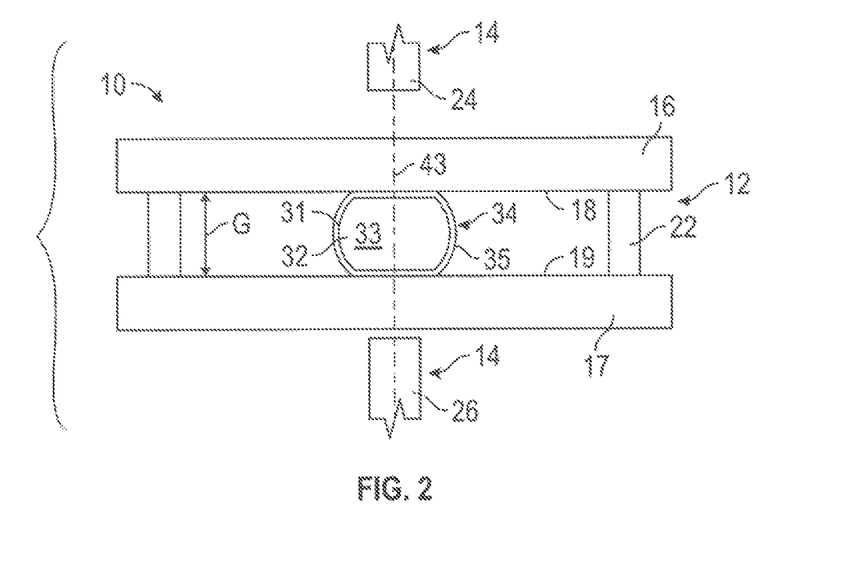
FIG. 2 is a cross-sectional side view of the bubble analysis apparatus of FIG. 1 with the plates being moved closer together so as to compress the bubble therebetween.

The bubble holding mechanism 12 includes a first plate 16 and a second plate 17. The first plate 16 is a planar plate with an interior bubble engagement surface 18 disposed in a flat plane. The first plate 16 also has an exterior surface 20 disposed in a flat plane parallel the engagement surface 18. The second plate 17 is similar having an interior bubble engagement surface 19 disposed in a flat plane and an exterior surface 21 disposed in a flat plane parallel to the flat plane of the bubble engagement surface 19. In FIG. 2, when engaging a bubble 30 for analysis, the first plate 16 and the second plate 17 are disposed parallel to each other. One or more spacers 22 are provided carried on the second plate 17 and extending from the second plate 17 toward the first plate 16. Each of the spacers 22 extend from the second plate 17 the same distance and present distal ends 23 disposed in a flat plane parallel to the second plate 17.

Figure 1:
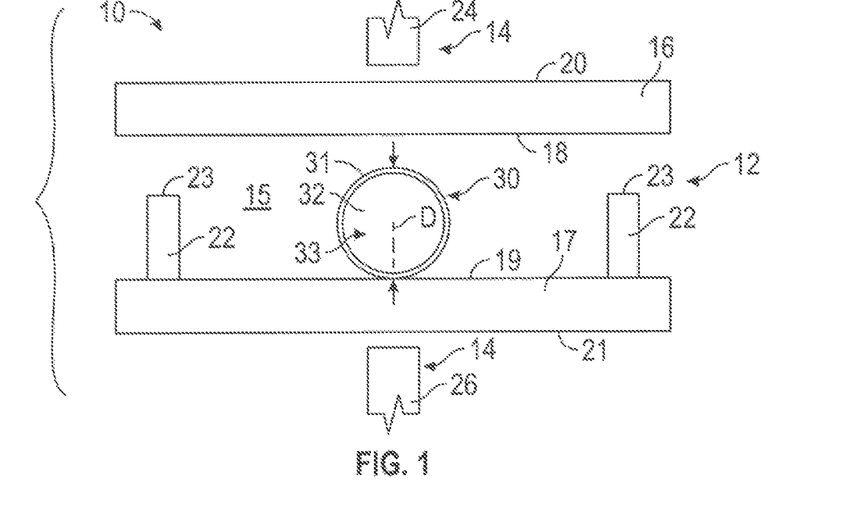
FIG. 1 is a schematic cross-sectional side view of a first embodiment of a bubble analysis apparatus in accordance with the present invention showing a single bubble positioned between two spaced plates.

As seen in FIG. 1, a single bubble 30 is shown supported on the second plate 17 in a gap 15 between the surface 18 of the first plate 16 and the surface 19 of the second plate 17 with the first plate 16 spaced from the bubble 30. The bubble 30 has a bubble wall 31 defining and forming therein a bubble interior compartment 32 enclosing a gas 33 therein. The bubble wall 31 is formed from a foamable liquid such as water and a surfactant. The bubble wall 31 is generally spherical as seen in FIG. 1. The bubble wall 31 has an exterior bubble diameter schematically illustrated as D.

Figure 4:
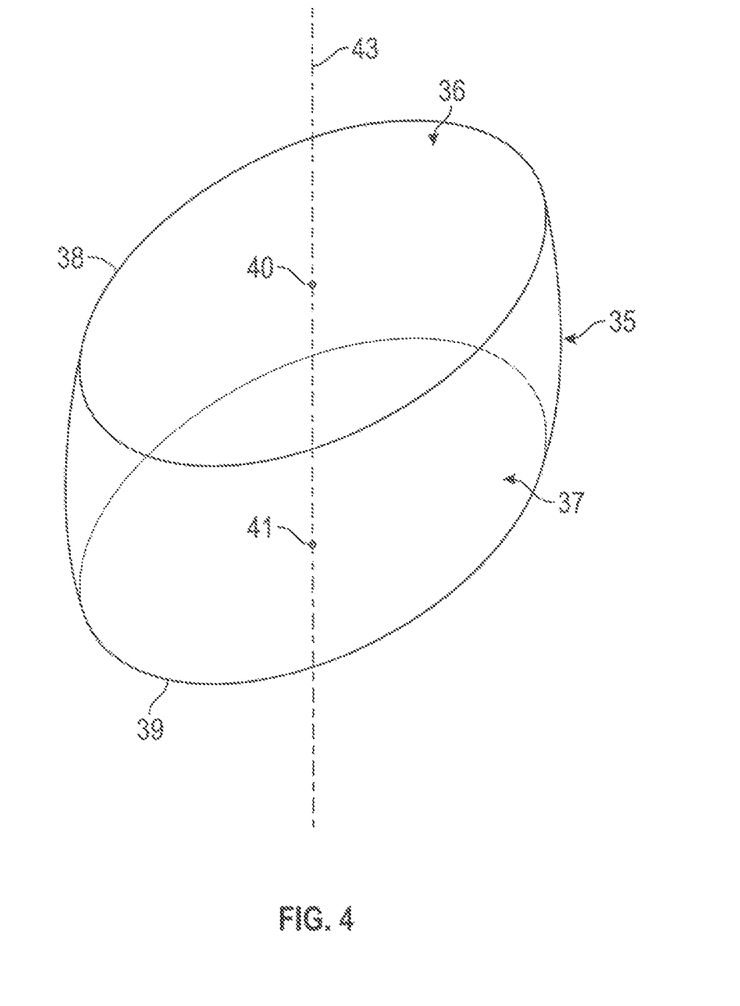
FIG. 4 is a schematic pictorial view of the compressed bubble of FIG. 2.

In use of the bubble analysis apparatus 10, a bubble 30 is placed between the first plate 16 and the second plate 17 as illustrated in FIG. 1 and, subsequently, as illustrated in FIG. 2, the first plate 16 and the second plate 17 are moved towards each other until the spacers 22 engage the first plate 16 and thus locate the first plate 16 and the first plate 17 spaced by the gap 15 as reduced to the gap spacing distance G compressing the spherical bubble 30 between the first plate 16 and the second plate 17 and providing the bubble 30 in a compressed state as a compressed bubble 34. As can be seen in FIG. 4, the compressed bubble 34 has a generally disc-shaped compressed bubble wall 31 including an annular equatorial wall portion 35 spanning between the first plate and the second plate and bridging between a first polar end wall portion 36 adjacent the first plate 16 and a second polar end wall portion 37 adjacent the second plate 17. As seen in FIG. 2, the bubble 30 remains intact, that is, with its bubble wall 31 intact maintaining the bubble interior compartment 32 with the gas 33 constrained inside.

The compressed bubble 34 is compressed between the bubble engagement surface 18 of the first plate 16 and the bubble engagement surface 19 of the second plate 17. With compression of the bubble, the first polar end wall portion 36 comes to lie adjacent the bubble engagement surface 18 with the first polar end wall portion 36 substantially in the flat plane of the bubble engagement surface 18 and with the first polar end wall portion 36 having a circular perimeter 38 disposed about a central point 40 of the generally circular polar first end wall portion 36.

Similarly, the second polar end wall portion 37 lies in the plane of the bubble engagement surface 20 of the second plate 17 with a circular perimeter 39 disposed about a center point 41.

The annular equatorial wall portion 35 bridges between the circular perimeters 38 and 39 of the first and second polar end wall portions 36 and 37. The annular equatorial wall portion 35 is approximately frusto-spherical with a convex outwardly directed surface. The center point 40 of the first polar end wall portion 36 and the center point 41 of the second polar end wall portion 37 lie along a central axis 43 normal the flat plane in which the first plate 16 and the second plate 17 lie and the first polar end wall portion 36 and the second polar end wall portion 37 have their circular perimeters 38 and 39 effectively aligned coaxially about the center axis. The compressed bubble 34 has a flattened disc-like shape and appearance as seen in FIGS. 2 and 4.

The optical analysis system 14 is illustrated by a schematic emitter 24 disposed opposed to the exterior surface 20 of the first plate 16 and a schematic sensor 26 disposed opposed to the exterior surface 21 of the second plate 17.

The optical analysis system 14 emits light from the schematic emitter 24 to pass through the first plate 16, the compressed bubble 34 and the second plate 17 which light is to be received by the schematic sensor 26. The notional sensor 26 is adapted to measure the properties of the light as passed through the compressed bubble 34. The optical analysis system 14 includes components not shown on FIG. 2 to compare the properties of the light sensed by the sensor 26 with properties of the light emitted by the notional emitter 24. The properties of the light emitted by the emitter 24 can be determined by analysis of the light emitted or by preknowledge of the nature of the light to be emitted by a specific emitter. The differences in the properties of light as passed through the compressed bubble 34 and the properties of light emitted can be used in a known manner to estimate based on the differences the chemical composition of the bubble, particularly an estimate of the chemical composition of the gas 33 within the bubble.

The bubble holding mechanism 12 advantageously provides for the passage of light parallel to the central axis 43 through the first polar end wall portion 36 and the second polar end wall portion 37 so as to minimize scattering and defraction of the light on passing through the first polar end wall portion 36 and the second polar end wall portion 37. Preferably, although not necessary, each polar end wall portion is substantially flat and lies in common parallel planes. Each of the first plate 16 and the second plate 17 are preferably formed of a material that suitably permits the emitted light to pass therethrough. Preferably, the exterior surfaces 20 and 21 of the plates and the bubble engagement surfaces 18 and 19 are all disposed parallel toward minimizing scattering and diffusion of the light emitted on passing through the plates.

The gap or plate spacing distance G that the first plate 16 and the second plate 17 are spaced representing the distance between the bubble engaging surface 18 and the bubble engaging surface 19 is preferably selected having regard to a bubble desired to be analysed. As shown in FIG. 2, the bubble 30 is compressed between the first plate 16 and the second plate 17. Thus, the gap distance G is selected to be less than the bubble diameter D. The relationship between the bubble diameter D and the gap spacing distance G is selected so as to provide the first polar end wall portion 36 and the second polar end wall portion 37 with an area which is adequate for the passage of light between the emitter 24 and the sensor 26. The gap spacing distance G can be selected having regard to a number of factors. The gap spacing distance G needs to be selected so as to not be so small as to rupture the bubble 30 in compression of the bubble 30. Preferably, the gap spacing distance G is in the range of 50% to 95% of the diameter, more preferably, in the range of 50% to 70% of the diameter D. There is, however, no limit to the ratio of the gap spacing distance G to that of the diameter D of the spherical bubble 30 provided that the first and second polar end wall portions 36 and 37 have an area of a size that facilitates passage of light from the emitter 24 to the sensor 26 and the compressed bubble does not rupture during compression.

As to the nature of the emitted light emitted by the emitter 24, the selection of such light to have suitable properties is readily made by a person skilled in the art. Preferably, the emitted light is directed through the first plate 16 normal to the plane in which the first plate lies towards reducing scattering and diffusion as the light passes through the bubble and plates. The emitted light may preferably be polarized. The emitted light may preferably be emitted by a laser as to provide parallel rays of light.

Figure 5:
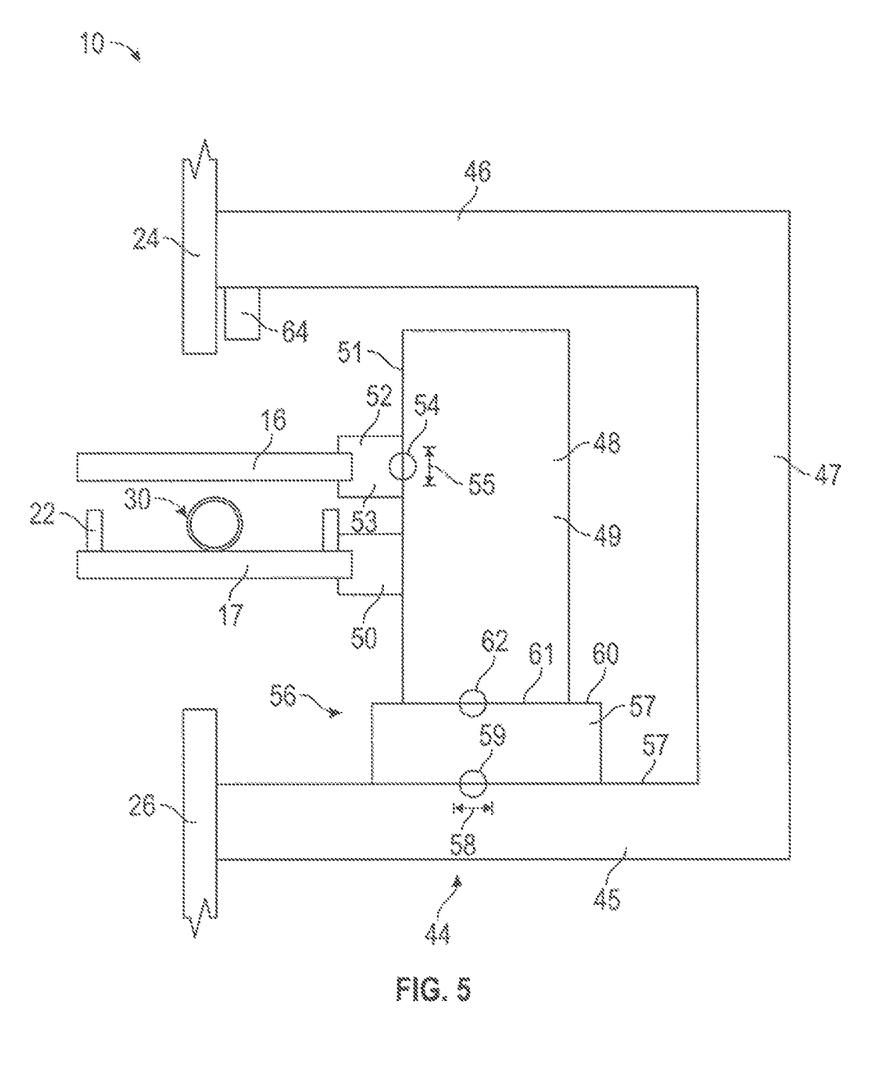
FIG. 5 is a schematic side view of the bubble analysis apparatus of FIG. 1 showing additional components.

Reference is made to FIG. 5, showing the apparatus of FIG. 1 with additional components forming the bubble analysis apparatus 10. As shown in FIG. 5, the optical analysis system 14 includes an optic holding structure 44 schematically shown in side view as being U-shaped with a lower support arm 45 and an upper support arm 46 supported spaced from each other by a support pillar 47. The schematic emitter 24 is carried by the upper support arm 46 and the schematic sensor 26 is carried by the lower support arm 45.

FIG. 5 shows a plate holding structure 48. The plate holding structure 48 has a vertically extending tower 49. The plate holding structure 48 is shown as having the second plate 17 fixedly secured to a second plate coupling portion 50 on the left side of the tower 49 with the second plate 17 extending horizontally to the left from the tower 49. The tower 49 has a vertical surface 51 facing to the left above the second plate 17. A first plate coupling portion 52 is provided by a vertical slide member 53 vertically slidably mounted to the vertical surface 51 for movement vertically relative to the tower 49 by a first drive mechanism 54 providing for relative movement in the direction indicated by the arrow 55. The first plate coupling portion 52 and the slide member 54 carry and fixedly support the first plate 16 for relative vertical movement of the first plate 16 relative the second plate 17 preferably maintaining the first plate 16 and the second plate 17 parallel.

A positioning arrangement 56 is provided to adjust the relative locations of the plates 16 and 17 as carried by the plate holding structure 48, on one hand, and the optical holding structure 44 on the other hand. The lower support arm 46 of the optical holding structure 44 has a horizontal upper surface. A slide block 57 is slidably mounted to the upper surface for sliding horizontally to the left or right as indicated by arrow 58 and controlled by a second drive mechanism 59 schematically shown. The slide block 57 has a horizontal upper surface 60. The tower 49 has a horizontal lower surface 61. The tower 49 is slidably mounted to the upper surface 60 for sliding into or out of the plane of the drawing sheet and controlled by a third drive mechanism 62 schematically shown.

Figure 3:
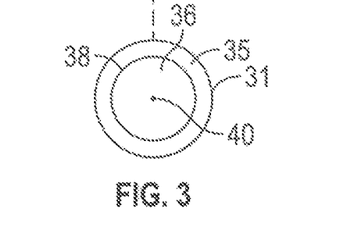
FIG. 3 is a schematic top view of the compressed bubble shown in FIG. 2.

In use of the apparatus shown in FIG. 5, with the first plate 16 spaced from the second plate 17, one or more bubbles 30 are placed between the plates. Subsequently, the first drive mechanism 54 moves the vertical slide member 53 so as to move the first plate 16 down into engagement with the spacers 22 to locate the first plate 16 and the second plate 17 spaced the desired gap spacing distance G and compress the bubble 30 therein to form a compressed bubble 34 as shown in FIG. 2. On FIG. 5, a camera 64 is shown carried on the upper support arm 46. In use of the embodiment illustrated in FIG. 5, one or more bubbles 30 are placed on the second plate 17 and compressed to form the compressed bubble 34. The camera 64 is directed downwardly and can view the one or more bubbles 30 in their compressed state through the first plate 16. Each compressed bubble 34 would appear to the camera in top view as seen in FIG. 3. The camera can be used to determine the location of the first polar end wall portion 36 and to thereby estimate the location of the center position 40 of the first polar end wall portion 36. With this information, a controller of a control system, not shown, can control the second drive mechanism 59 and the third drive mechanism 62 to relatively position the plate holding structure 48 and the optic holding structure 44 that the center position 40 is directly below the emitter 22, that is, with the center axis 43 through the compressed bubble 34 to be coaxially aligned with light to be emitted from the emitter 24 to the sensor 26.

In accordance with the present invention, a foam of a foaming liquid and a gas can be generated and a portion of this foam including a plurality of bubbles typically in multiple layers is placed on the lower plate 16 of the apparatus as illustrated in FIG. 5. The bubbles of the foam are then compressed between the first plate 16 and the second plate 17 to effectively form a single layer of bubbles, at least a single layer of bubbles in a particular range of a bubble diameter with the gap spacing distance G selected to be a suitable distance having regard to, for example, the average or mean diameter of the bubbles in the foam or at least having regard to an expected or desired diameter of a bubble whose composition is to be measured.

Figure 6:
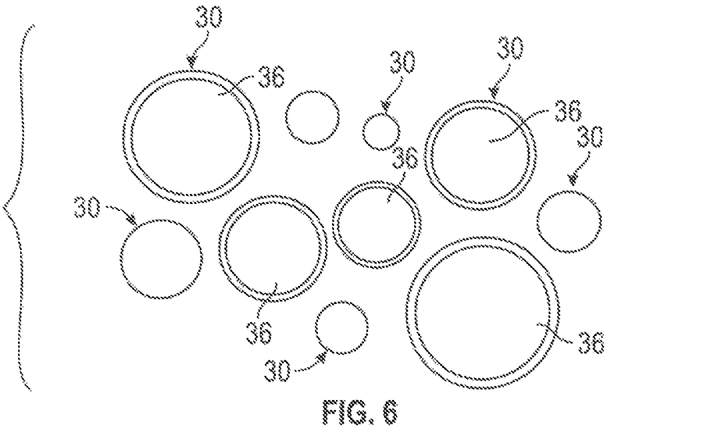
FIG. 6 is a schematic top view of a plurality of different size bubbles between the plates of the bubble analysis apparatus in FIG. 5.

FIG. 6 illustrates a top view as seen by the camera 64 of a plurality of bubbles from the foam as compressed between the plates 16 and 17 when the plates are spaced by the gap spacing distance G. The camera 64 can view the bubbles and data from the camera 64 can be used by a controller to make a selection of a suitable bubble for analysis based on the area of the first polar end wall portion 36 of the bubble and selecting a bubble having regard to a range of diameters for a desired sized bubbles to be analysed and a relationship between the area of the first polar end wall portion 36 and the diameter of each bubble. Thus, a suitable compressed bubble 34 can be selected to be analysed and the controller can relatively move the plate holding structure 48 and the optic holding system 44 to a suitable position that the emitter 24 and sensor 26 will be coaxially aligned with the center portion 40 of the selected compressed bubble 34 to be analysed.

FIG. 6 illustrates an image of various bubbles as seen by the camera 64. The controller is able from the image to visually differentiate between bubbles which are compressed between the plates 16 and 17 and those which are not compressed as by determining the area of the polar end wall portions with knowledge of the gap spacing distance G. Various algorithms can be developed to distinguish between bubbles and select a suitable bubble that is compressed as a bubble desired to be analysed.

In accordance with the embodiment of FIG. 5, when a plurality of bubbles are viewed by a camera, insofar as more than one bubble may be desired to be analysed, the plate holding structure 48 can be moved to a first location relative the optic holding system 44 to analyse a first bubble and, subsequently, to a second location to analyse a second bubble and, subsequently, to a third and subsequent locations to analyse third and subsequent bubbles.

Figure 7:
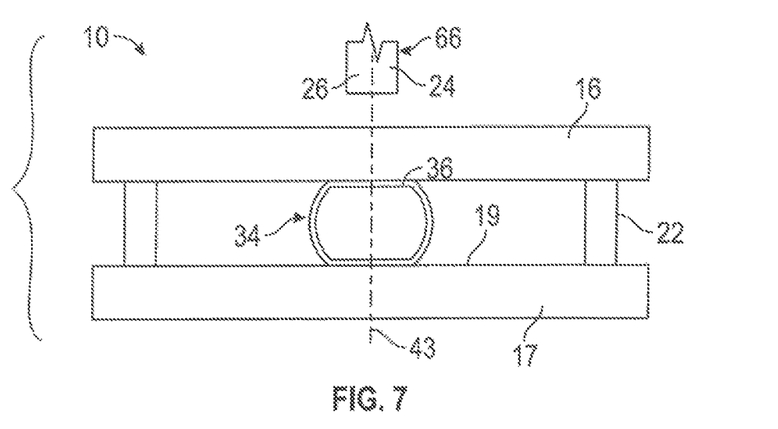
FIG. 7 is a cross-sectional side view similar to FIG. 2 of a second embodiment of a bubble analysis apparatus.

Reference is made to FIG. 7 which is a view of a second embodiment of a bubble analysis apparatus 10 having substantially the same as the apparatus in FIG. 2, however, with the exceptions that the bubble engaging surface 19 of the second plate 17 is mirrored and that an optical device indicated as 66 serves as both the emitter 24 and the sensor 26. In the embodiment of FIG. 7, light from the emitter 24 passes through the first plate 16 through the compressed bubble 34 and is reflected from the second plate 17 to pass back through the compressed bubble 34 and through the first plate 16 to the sensor 26. In the embodiment of FIG. 7, the second plate 17 need not be of a material that permits light to pass therethrough. In a preferred configuration, however, the optical device 66 carries not only the emitter 24 and the sensor 26 but also serves as the camera 64. However, in the embodiment of FIG. 7, if the plate 17 can permit light to pass therethrough, it may provide for a convenient location of the camera 64 underneath the second plate 17.

Figure 8:
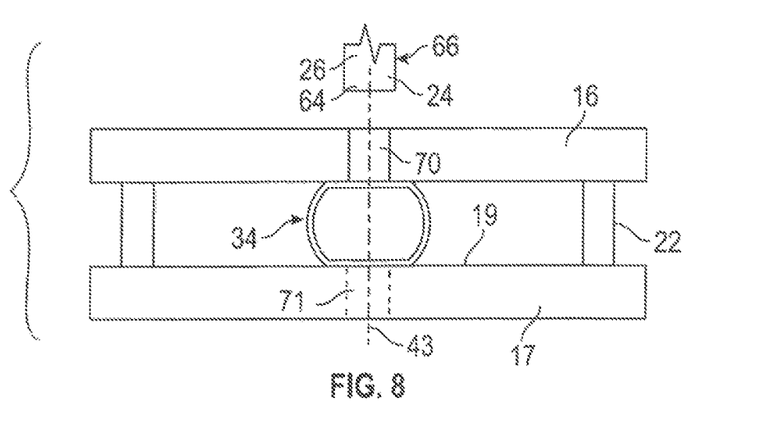
FIG. 8 is a cross-sectional side view similar to FIG. 2 of a third embodiment of a bubble analysis apparatus.

Reference is made to FIG. 8 which illustrates a third embodiment of the bubble analysis apparatus 10 similar to that shown in FIG. 7. The embodiment of FIG. 8 differs from the embodiment of FIG. 7 in that an opening 70 is provided through the first plate 16 through which light may pass without absorption of a spectra of the light. As illustrated in FIG. 8, the opening 70 is to be located preferably coaxially about the center axis 43 of the compressed bubble 34. An advantage of the embodiment of FIG. 8 is that the plate 16 can be made from a material without regard to the transmission properties of the material regarding the light that is emitted and sensed. In the embodiment of FIG. 8, as in FIG. 7, light is reflected from a mirrored surface of the second plate 17. Nevertheless, preferably one of the first plate 16 or the second plate 17 will be selected to permit light to pass therethrough such that a camera 64 may view the bubble between the plates.

The opening 70 is preferably of a diameter as shown on FIG. 8 which is less than the diameter of the first polar end wall portion 36 such that the first polar end wall portion 36 will, due to engagement with an annular portion 71 of the bubble engagement surface 18 about the opening 70, engage the compressed bubble 34 so as to have the first polar end wall portion 36 substantially lie in a flat plane that avoids deflection of light passing therethrough.

In the embodiment of FIG. 8, to facilitate the relative location of a bubble on the first plate 16 with the opening 70 coaxially above a center point of the first polar end wall portion 36, the first plate and the second plate may be mounted for relative horizontal left to right and front to back movement as may be accomplished by various mechanisms for relative movement of the first plate 16 and the second plate 17 towards relative movement of the plates and the bubble to achieve the desired orientation. The movements may be guided by the camera 64 sensing the bubble compressed conditions. Preferably, a plurality of such openings 70 may be provided and placing a plurality of bubbles between the plates can provide such a probability there will be relative alignment of at least one desired bubble with one of the openings.

In a modification of the apparatus shown in FIG. 8, an optional opening 71, shown in broken lines that is similar to opening 70, could be provided through the second plate 17 coaxially aligned with the opening 70 with the sensor 26 to be located below the second plate 17.

Figure 9:
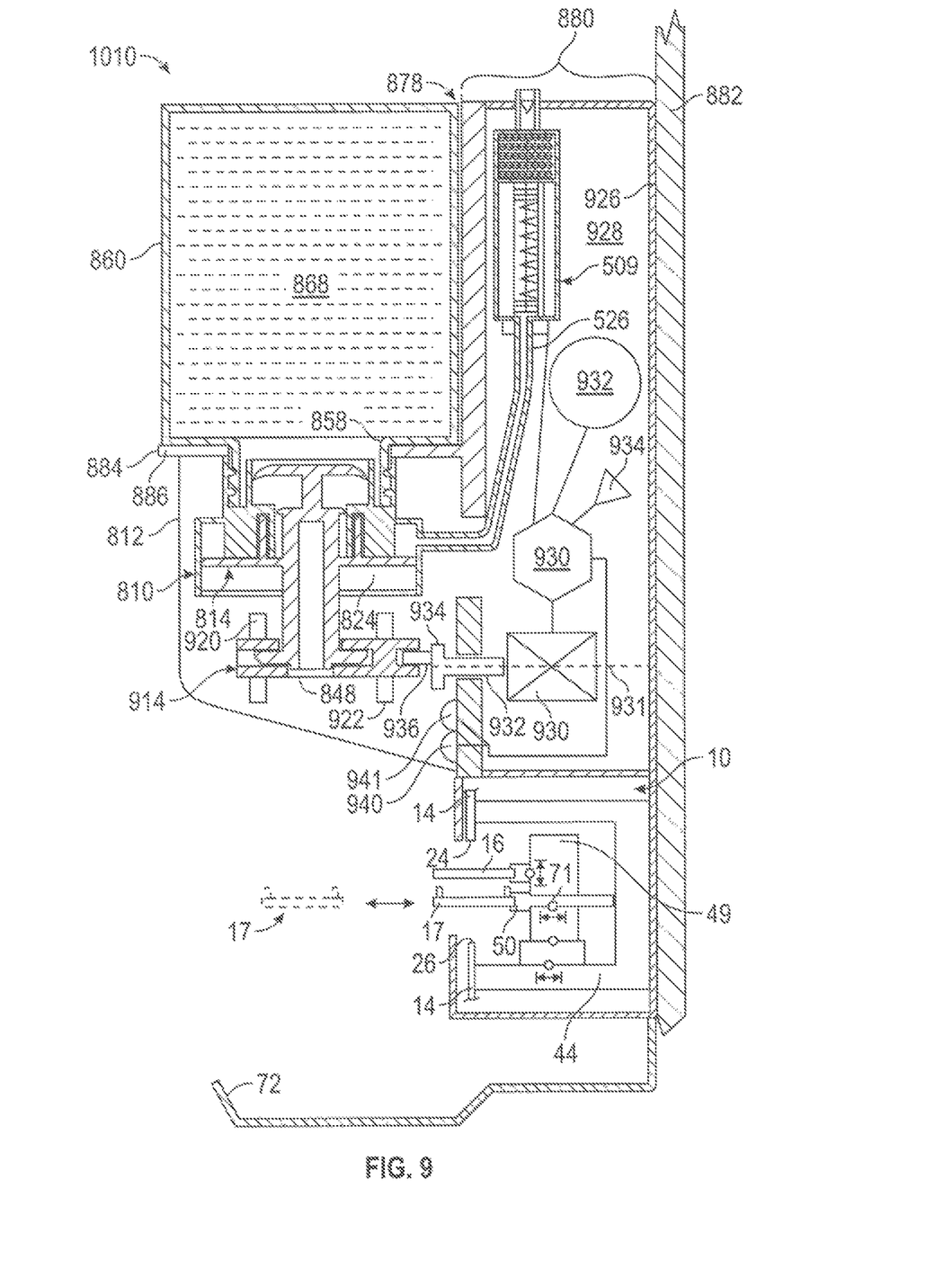
FIG. 9 is a schematic cross-sectional of a first embodiment of a hand cleaner dispenser in accordance with the present invention.

Reference is made to FIG. 9 which illustrates a dispenser 1010 which is preferably a dispenser of hand cleaner. The dispenser 1010 is the same as that illustrated in U.S. Pat. No. 9,936,841 to Ophardt et al, issued Apr. 10, 2018 for dispensing an ozonated foam, however, includes, additionally, a bubble analysis apparatus 10. As seen on FIG. 9, the bubble analysis apparatus 10 is shown merely schematically as mounted to a housing 878 for the dispenser 1010. The bubble analysis apparatus 10, shown on FIG. 9, is substantially identical to that shown in FIG. 5 but for the modifications that includes second plate 17 horizontally movable to an extended position as shown in dashed lines on FIG. 9. As disclosed in U.S. Pat. No. 9,936,841, the disclosure of which is incorporated herein by reference, ozone gas generated in an ozone generator 509 and a foamable liquid 868 from a reservoir 860 are simultaneously discharged by a piston pump 810 to pass through a foam generator and downwardly out a discharge outlet 848 as onto a user's hands for use. In order to obtain a sample of the ozonated foam, the second plate 17 is adapted to be moved horizontally from within the bubble analysis apparatus 10 towards the left as seen in FIG. 9 underneath the discharge outlet 848 such that the ozonated foam or at least some of the foam becomes deposited on the surface 19 of the second plate 17. The second plate 17 is then moved to a retracted position within the bubble analysis apparatus 10 for analysis. The movement of the second plate 17 between the retracted position and the extended position is shown as accomplished by the second plate coupling portion 50 being mounted to the tower 49 for sliding horizontally as controlled by a fourth drive mechanism 71.

Referring to FIG. 9, at the bottom of FIG. 9, a drip tray 72 is shown located below the discharge outlet 848 to catch dispensed foam not caught by a user's hand. The bubble analysis apparatus 10 may be mounted to or within the drip tray 72 rather than directly to the housing 878.

In a dispenser as shown and described with reference to FIG. 9, the bubble analysis apparatus 10 may be controlled and powered by the same controller 930 and power source 934 as a remainder of the dispenser 1010. The dispenser 1010 preferably has the ability to analysis the bubble composition. The results of any determinations of the bubble composition can be used as feedback towards calibrating the dispenser 1010 and controlling and monitoring its operation including operation of the ozone generator 509 and the pump 810 in a manner to provide for optimized ozonated foam and particularly ozonated foam having concentrations of ozone gas within the bubbles of the foam within desired ranges.

In the embodiment of FIG. 9, the optical analysis system 14 is preferably a simplified arrangement in which the emitter 26 comprises a light emitting diode selected to emit light of a wavelength that is absorbed by ozone gas and preferably comprising light having a wavelength in the range of about 200 nm and 310 nm and, preferably, of a wavelength of 250 nm. The sensor 26 is preferably a sensor which senses the intensity of the light in the wavelengths emitted and from measure of the intensity of the optical analysis system 14 can make an assessment as to the concentration of ozone within the gas in the bubble.

Various other arrangements can be established for foam that is dispensed by the dispenser to be placed between the plates 16 and 17 for analysis.

Preferably, the bubble analysis apparatus 10 includes an arrangement or mechanism for cleaning the plates 16 and 17 in contact with the bubbles as, for example, by discharging water from one or more jets onto the plates and catching the discharged water as in a drain. The water may be provided as, for example, from a reservoir on a dispenser or from a water supply system in a building. During use of water, an air jet may be used to remove the bubbles and their residue and/or an alcohol based liquid may be used which will evaporate without leaving a residue.

Spectroscopic methods for analysis of matter by passing light through liquids and/or gases are known to persons skilled in the art and it is the scope of the person skilled in the art to select suitable arrangements for measuring properties of the gas in the bubbles as by optical spectroscopic methods, for example, by analysis of light that passes through the bubble as contrasted with the light that is emitted.

Preferably, the methods of analyzing the gas in a bubble is selected from spectroscopic methods and preferably optical spectroscopy using various methods and instruments as are known to persons skilled in the art. However, other methods of spectroscopy may be used. Various spectroscopic methods and apparatuses for use are disclosed in the following website, the disclosure of which is incorporated herein by reference:

chem.libretexts.org/Bookshelves/Analytical_Chemistry/ Book%3A_Analytical_Chemistry_20_(Harvey)/10_Spectroscopic_Methods. Jul. 25, 2019.

Preferred spectroscopy is optical spectroscopy and preferably absorption spectroscopy in which a beam of electromagnetic radiation passes through the bubble with selected wavelengths that radiation intensity is attenuated with such attenuation referred to as absorption. Various different apparatus may be used for optical spectroscopy notably involving the use of light including ultraviolet, visible and infrared light in spectroscopic methods and apparatus. The particular nature of the apparatus to be used for such spectroscopy is not limited, however, can include simple instruments such as filter photometers, single-beam spectrophotometers, double-beam spectrophotometers and diode spectrometers including diode array spectrometers. For example, in the context of analysis for ozone gas, a diode spectrometer with a single detector can be used to monitor one wavelength, however, multiple diodes can be used to monitor multiple wavelengths.

As but one example of a spectrometer which can be used is the hand-held spectrometer disclosed in U.S. Pat. No. 7,236,243 to Beecroft et al, issued Jun. 26, 2007, the disclosure of which is incorporated herein by reference. The applicant has appreciated that relatively simple spectrometers having features the same as or more simplistic to those as disclosed in U.S. Pat. No. 7,236,243 can be incorporated into a device to analyze the gas in the bubble in accordance with the present invention and can, for example, be modified as for incorporation into a dispenser as in replacement of the schematic spectrometer schematically illustrated in the various figures in this application and, notably, FIG. 9.

Figure 10:
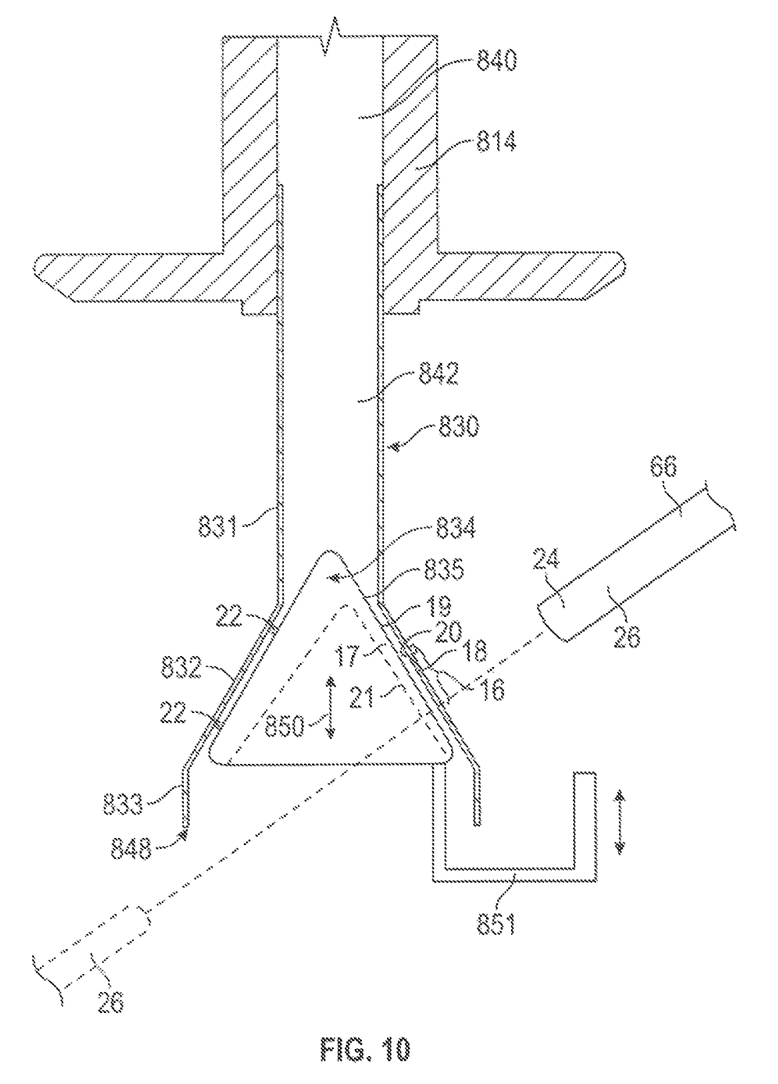
FIG. 10 is a schematic cross-sectional front view of a second embodiment of a bubble analysis apparatus in accordance with the present invention.

Reference is made to FIG. 10 illustrating a schematic cross-sectional front view of a fourth embodiment of a bubble analysis apparatus in accordance with the present invention. In FIG. 10, the lower discharge end of the piston 814 shown in FIG. 9 is illustrated as modified so as to carry, fixed thereto, a hollow extension tube 830 open at a lower end at a new discharge outlet 848. The tubular extension 830 includes a cylindrical upper portion 831, a frustoconical intermediate portion 832 and a discharge portion 833. The frustoconical lower portion 832 has a side wall that increases in diameter downwardly. The frustoconical portion 832 merges with the cylindrical discharge portion 833.

The frustoconical portion 832 has an interior bubble engagement surface 18 disposed in a flat plane and an exterior surface 20 disposed in a flat plane parallel to the bubble engagement surface 18. As indicated on FIG. 9, an area of the frustoconical portion 832 provides what may be considered a first plate 16 with suitable optical properties.

Disposed within the extension tube 830 is a diverting plug 834 which is shown in the illustration as being frustoconical and providing an interior bubble engagement surface 19 opposed to the interior bubble engagement 18 of the first plate 16. The interior bubble engagement surface 19 is preferably disposed in a flat plane parallel to the flat plane of the bubble engagement surface 19.

The plug 834 is preferably coaxially located within the frustoconical portion 832 of the extension tube 830 with the interior bubble engagement surface 19 spaced at a desired distance from the interior bubble engagement surface 18 as may be accomplished, for example, with the assistance of spacers 22 carried on the plug 834 at a plurality of annular locations so as to provide the desired spacings yet not prevent flow of foam between the extension tube 830 and the plug 834. For convenience, the spacers 22 are only shown on the left hand side of FIG. 10.

In an operation of the device, foam that is generated is passed through a central passageway 840 of the piston 814 down through a central passageway 842 of the extension tube 830, and annularly about the plug 834 between the plug 834 and the extension tube 830 to exit out the discharge outlet 848. The configuration of the interior surfaces 18 and 19 of the extension tube 830 and the plug 834 are provided such that as foam passes between the extension tube 830 and the plug 834, the foam will be substantially reduced to a thin layer of foam preferably reduced to substantially a single layer of bubbles which single layer of bubbles moves to be between the first plate portion 16 and is at least constrained and preferably compressed such that spectroscopic analysis of one or more of the bubbles and, notably the gas within the bubble, may be carried out. Preferably, spectroscopic analysis is made of one or more bubbles while they are stationary as between strokes of the piston pump.

In the embodiment illustrated in solid lines in FIG. 10, as in the embodiment of FIG. 7, an optical device 66 is provided which serves both as an emitter 24 and as a sensor 26 with the first plate 16 permitting light from the emitter 24 to pass therethrough with the plug 834 serving as a plate whose interior bubble engagement surface 19 is mirrored and reflects light from the emitter 24 back to the sensor 26. While not shown, a desired optional camera can be provided as in the other embodiments so as to provide for appropriate relative location of the optical device 66 relative to one or more bubbles in the passageway between the first plate 16 and the plug 834.

Preferably, the plug 834 is provided to be mounted for relative movement relative to the extension tube 830 for coaxial movement as in a direction indicated by the arrow 850. By moving the plug 834 axially outwardly, the space between the opposed interior surface 18 and the interior surface 19 can be increased so as to significantly reduce the resistance to flow of foam through the tube extension 830 to the discharge outlet 848. As but one example, the plug 834 may be mounted on a support arm 851 which extends axially through the discharge outlet 848 and then radially for mounting in a manner, not shown, to the piston 841 for relative movement of the plug 834 relative to the piston 814.

As an optional optical arrangement, as shown on the plug 834 in a broken line of attenuating dashes and dots, the plug 834 may be cut away so as to have a hollow interior open downwardly at an opening effectively providing a second plate 17 with an exterior surface 21 such that light from the emitter 24 may pass through the first plate 16, a bubble, the second plate 17 and through the hollow interior of the plug 834 and out the downward opening of the plug 834 to a sensor 26 shown in broken lines below and to the right of the plug 834, in which case, it is to be appreciated that the interior bubble engagement surface 19 of the second plate 17 would permit light to pass therethrough.

While FIG. 10 shows an arrangement in which the plug 834 is axially slidable to different positions within the extension tube 830, it is to be appreciated that mechanical arrangements could be provided to withdraw the plug 834 totally from the extension tube 830 as, for example, by moving it axially downwardly and then radially to one side.

The arrangement in FIG. 10 shows fluid flow merely annularly about the plug 834 between the plug 834 and the extension tube 830. This is not necessary. For example, a central passageway could be provided through the plug 834 such as providing for flow not only through the central passageway but also between the plug 834 and the first plate 16, in which case, there may not be a need for the plug 834 to be movable relative to the extension tube 830. The plug's central passageway could have a valve to change flow therethrough.

In the embodiment illustrated in FIG. 10, the frustoconical portion 832 is shown to be frustoconical and the exterior bubble surface 19 of the plug 835 is also shown to be frustoconical. Neither is necessary and the portion 832 and its surface 18 and/or the surface 19 may have other shapes. The relative shapes of the interior surface 19 of the portion 832 and the exterior surface 19 of the plug 835 are preferably chosen so as to achieve a number of objectives. The principal objective is to provide an arrangement whereby a mass of foam that is discharged come to be funneled and directed to flow to between a viewing portion where spacing of the surface 18 and the surface 19 advantageously reduces the foam to being constrained within a space, preferably, to comprising a single layer of bubbles which is advantageous for spectroscopic analysis. In FIG. 10, the distance between the surfaces 18 and 19 is constant, however, this is not necessary. Thus, the distance between the surfaces 18 and 19 may, for example, reduce gradually as they extend downwardly to where the bubbles are located for optical viewing and, similarly after optical viewing, may increase gradually.

Such a decrease in the spacing between the inside surfaces 18 and 19 of the extension tube 830 and the plug 834 is preferably one which will assist in maintaining the bubbles unbroken yet provide them as between the surfaces 18 and 19 in an optical viewing area in a form suitable for optical spectroscopy.

In FIG. 10, the surfaces 18 and 19 are shown spaced a constant distance. However, the radially outwardly directed surface 18 of the plug 834 extends radially outwardly as it extends downwardly from an upper apex of the plug 834 and thus reduces the radial extent of an upstream annular spacing portion between the surface 18 of the plug 834 and an interior surface of the cylindrical upper portion 831. Foam passes through such upstream annular spacing portion to flow downstream and enter between the first surface 18 and the second surface 19. In such flow, the upstream annular spacing portion funnels the foam into between the first surface 18 and the second surface 19.

In accordance with some embodiments of the present invention, it is preferred that a bubble is compressed between the plate 16 and the plate 17 for viewing, however, this is not necessary. In the context of an arrangement, such as shown in FIG. 10, it is possible that the bubbles are constrained preferably between the surfaces 18 and 19 as in a single layer of bubbles or as in a spacing which provides for possibly a small number of layers of bubbles, possibly one or two or three or five or some relatively small number, for example, preferably less than 10. The surfaces 18 and 19 may accordingly be selected so as, for example, to accommodate the movement of the foam between them so as to constrain the foam to a desired number of possible layers of bubbles, having regard to a desired bubble diameter that may be selected having regard to the nature of the foam to be generated. For example, a desired bubble diameter may be selected to be a median of desired bubble diameters. The first plate and the second plate may, for example, be spaced a distance not greater than 200% or 300% or 500% or 1000% of a median diameter of the bubbles.

Towards accommodating any defraction or refraction or bending of the light that may be emitted to pass through the bubbles to a sensor, particularly when the bubbles are in a plurality of bubbles, a broad array of sensors could be provided, for example, substantially encircling the gas bubbles which are radiated so as, for example, to capture all of the light that passes through any portions of the bubbles and calculations may be performed having regard to the total light emitted and the light sensed which could provide a correlation as to the level of a gas, for example, ozone, in bubbles captured over an area between the spaced surfaces 18 and 19.

An advantage of the embodiment illustrated in FIG. 10 is that with continued discharge of foam, the gap and the space between the surfaces 18 and 19 may be cleaned in normal operation of the dispensing apparatus by the flow of the foam through the space between the surfaces 18 and 19 to the discharge outlet.

Of course, in operation of the apparatus, for example, of FIG. 9 incorporating the arrangement of FIG. 10, the analysis of the ozone could be carried out in a step of operation of the pump to dispense foam at a time when a person's hand is not below the discharge outlet albeit possibly analysis could also be carried out at times when, in fact, the foam is being discharged onto a user's hand.

While the invention has shown and a preferred example is particularly adapted for measuring ozone gas in a bubble, it is to be appreciated that the method and apparatus can be adapted to measure and sense the presence of any gases or liquids within a bubble including within the liquid bubble wall and within the gas within the bubble. The method and apparatus are particularly adapted for use in sensing gases in bubbles which may have a relatively short half-life. While the method is advantageous for sensing a concentration of ozone gases within an ozonated foam for cleaning, it is within the scope of the present invention to form a bubble containing a gas merely for the purposes of analysis of the gas without the gas containing bubble having any other particular purpose.

While the invention has been described with reference to preferred embodiments, many modifications and variations will now occur to a person skilled in the art. For a definition of the invention, reference is made to the following claims.

I claim:

1. A method of optically assessing a chemical composition of a bubble comprising the steps of:
    a) generating the bubble having a liquid bubble wall forming a bubble interior compartment enclosing a gas, wherein the bubble is generated as a spherical bubble with the bubble wall being spherical and having an exterior bubble diameter,
    b) locating the bubble in a gap formed between a first surface and an opposing second surface spaced a distance less than the bubble diameter with the bubble engaging both the first surface and the second surface,
    c) emitting electromagnetic radiation having at least one property,
    d) passing the emitted radiation through the bubble while the bubble is located in the gap to pass the emitted radiation through both the bubble wall and the bubble interior compartment,
    e) measuring the property of the emitted radiation after it has passed through the bubble,
    f) comparing the measured property of the emitted radiation after it passes through the bubble with the property of the emitted radiation before it passes through the bubble,
    g) estimating based on the results of the comparing step (f) the chemical composition of the bubble.

2. A method as claimed in claim 1 wherein:
    the said distance less than the bubble diameter is in a range of 60% to 90% of the bubble diameter.

3. A method as claimed in claim 2 wherein the second surface is parallel to the first surface.

4. A method as claimed in claim 3 including passing the emitted radiation through the bubble in a direction normal to the first surface.

5. A method as claimed in claim 3 including providing the surface of the second plate to have a mirrored surface that is reflective of the emitted radiation,
    directing the emitted radiation to pass through the first plate, through the bubble to reflect off the mirrored surface of the second plate and back through the bubble and through the first plate to provide emitted radiation that has passed through the bubble.

6. A method as claimed in claim 1 wherein:
    the step (b) includes locating the bubble in the gap formed between the first surface and the opposing second surface spaced the distance less than the bubble diameter with the bubble engaging both the first surface and the second surface with a first polar end wall portion of the bubble wall engaging the first surface lying in a plane of the first surface and a second polar end wall portion of the bubble wall engaging the second surface lying in a plane of the second surface with an annular equatorial wall portion of the bubble wall spanning between the first surface and the second surface and bridging between the first polar end wall portion and the second polar end wall portion.

7. A method as claimed in claim 6 wherein:
passing the emitted radiation in sequence through the first polar end wall portion of the bubble wall, through the bubble interior compartment and through the second polar end wall portion of the bubble wall.

8. A method as claimed in claim 6 including providing the gap between a first plate providing the first surface and a second plate providing the second surface,
providing the bubble between the first plate and the second plate while the first surface and the second surface are spaced a distance greater than the bubble diameter and moving the first plate and the second plate towards each other to locate the first surface and the second surface spaced the distance less than the bubble diameter compressing the bubble therebetween to form a compressed bubble with the first polar end wall portion of the bubble wall engaging the first surface lying in the plane of the first surface and the second polar end wall portion of the bubble wall engaging the second surface lying in the plane of the second surface with the annular equatorial wall portion of the bubble wall spinning between the first surface and the second surface and bridging between the first polar end wall portion and the second polar end wall portion.

9. A method as claimed in claim 8 including stopping movement of the first plate and the second plate towards each other to locate the first surface and the second surface spaced the distance less than the bubble diameter by engagement between one or more spacer members provided between the first plate and the second plate.

10. A method as claimed in claim 8 including locating on the first surface a center of the first polar end wall portion, and directing the emitted radiation to pass through the center.

11. A method as claimed in claim 10 including directing the emitted radiation to pass through the center by moving the first plate and the second plate while fixed together as a unit with the bubble compressed therebetween relative to an emitter for the emitted radiation such that the emitted radiation passes through the center.

12. A method as claimed in claim 6 including:
providing the gap between a first plate providing the first surface and a second plate providing the second surface,
moving the bubble in a downstream direction into the gap from an upstream portion between the first plate and the second plate in which the first plate and the second plate are spaced a distance greater than the bubble diameter thereby compressing the bubble as it is moved into the gap from the upstream portion.

13. A method as claimed in claim 12 including:
moving the bubble in the downstream direction between the first plate and the second plate from the gap toward a discharge outlet.

14. A method as claimed in claim 8 including:
providing the first plate to have a first opening therethrough circular about an axis, with the first opening having a first diameter about the axis not greater than ½ of the bubble diameter,
providing the compressed bubble between the first plate and the second plate with the first polar end wall portion coaxial about the axis, with the first polar end wall portion in engagement with the first plate annularly about the first opening,
directing the emitted radiation to pass through the through the first plate via the first opening.

15. A method as claimed in claim 14 including:
providing the second plate to have a second opening therethrough circular about the axis opposed to the first opening and the second opening having a second diameter about the axis not greater than ½ of the bubble diameter,
providing the compressed bubble between the first plate and the second plate and with the second polar end wall portion coaxial about the axis, with the second polar end wall portion in engagement with the second plate annularly about the second opening,
directing the emitted radiation to pass through the second plate via the second opening.

16. A method as claimed in claim 8 wherein the second surface is parallel to the first surface.

17. A method of optically assessing a chemical composition of a bubble comprising the steps of:
a) generating the bubble having a liquid bubble wall forming a bubble interior compartment enclosing a gas,
b) emitting electromagnetic radiation having a least one property,
c) passing the emitted radiation through the bubble to pass the emitted radiation through both the bubble wall and the bubble interior compartment,
d) measuring the property of the emitted radiation after it has passed through the bubble,
e) comparing the measured property of the emitted radiation after it passes through the bubble with the property of the emitted radiation before it passes through the bubble,
f) estimating based on the results of the comparing step (e) the chemical composition of the spherical bubble, including:
generating the bubble as one of a plurality of spherical bubbles each having its respective bubble wall of an exterior bubble diameter,
constraining the bubbles in a space formed between a first surface and an opposing second surface spaced a distance not greater than 10 times the diameters of the bubbles, and
passing the emitted radiation through the space while the bubbles are located in the space.

18. A method as claimed in any one of claims 1 to 17 to assess the presence of ozone within a bubble of a foamable aqueous fluid,
the emitted radiation including electromagnetic radiation of a wavelength that is absorbed by ozone, and
measuring radiation on of the wavelength of the emitted radiation after it has passed through the bubble,
comparing the measured radiation of the wavelength of the emitted radiation after it has passed through the bubble with the radiation of the wavelength of the emitted radiation before it passes through the bubble, and
estimating based on the results of the comparing the presence of ozone in the bubble.

19. A method as claimed in claim 18 including generating the bubble by passing a mixture of air containing ozone and the fluid through a foam generator to produce the bubble as part of a foamed mixture of the air containing ozone and the fluid.

20. A method of optically assessing the chemical composition of a plurality of bubbles comprising:

generating bubbles each having a liquid generally spherical bubble wall forming a bubble interior compartment enclosing a gas, the bubble wall having an exterior bubble diameter, constraining the bubbles between a first surface and a second surface, emitting electromagnetic radiation, directing the electromagnetic radiation emitted to pass through the bubbles, measuring differences in properties of the electromagnetic radiation that has passed through the bubbles compared to properties of the electromagnetic radiation emitted, estimated based on the differences measured, a chemical composition of the bubble, wherein the first plate and the second plate are spaced a distance selected from the group of:

not greater than 60% of a desired median exterior bubble diameter;

not greater than 200% of the median of the exterior bubble diameter;

not greater than 300% of the median of the exterior bubble diameter; and not greater than 1000% of the median of the exterior bubble diameter, including collecting electromagnetic radiation passing through the bubbles and comparing the intensity of a specific wavelength of electromagnetic radiation in the electromagnetic radiation emitted to the intensity of the specific wavelength of electromagnetic radiation in the electromagnetic radiation collected as a factor in estimating whether the bubbles include a compound that absorbs the specific wavelength of electromagnetic radiation.

* * * * *